United States Patent
Christensen (10) Patent No.: US 8,070,725 B2
(45) Date of Patent: Dec. 6, 2011

(54) LUER INTEGRATED AIR VENTING SYSTEM

(75) Inventor: Kelly D. Christensen, Centerville, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 473 days.

(21) Appl. No.: 12/192,293

(22) Filed: Aug. 15, 2008

(65) Prior Publication Data

US 2010/0042048 A1   Feb. 18, 2010

(51) Int. Cl.
*A61M 1/00* (2006.01)
(52) U.S. Cl. ...................................................... 604/122
(58) Field of Classification Search .................. 604/45, 604/122, 126, 533–537, 284, 164.01, 167.01, 604/167.02, 168.01, 256
See application file for complete search history.

(56) References Cited

U.S. PATENT DOCUMENTS

| 4,200,096 A | 4/1980 | Charvin |
| 4,935,010 A * | 6/1990 | Cox et al. ............... 604/122 |
| 5,290,246 A | 3/1994 | Yamamoto et al. |
| 2004/0181192 A1* | 9/2004 | Cuppy ...................... 604/256 |
| 2007/0043334 A1* | 2/2007 | Guala ....................... 604/533 |

FOREIGN PATENT DOCUMENTS

| WO | WO2008/058132 A2 | 5/2008 |
| WO | WO2008/058133 A2 | 5/2008 |

* cited by examiner

*Primary Examiner* — Christopher D Koharski
(74) *Attorney, Agent, or Firm* — Mony R. Ghose; Kirton & McConkie (57) ABSTRACT

A vascular access device incorporating a luer integrated air venting system, including a female luer fitting having a venting mechanism located within the female luer fitting and a fluid diverter located within the vent mechanism. The venting mechanism providing communication between said vascular access device and ambient surroundings until contact with a fluid.

20 Claims, 8 Drawing Sheets

LUER INTEGRATED AIR VENTING SYSTEM

BACKGROUND OF THE INVENTION

The present disclosure relates to infusion therapy with vascular access devices. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy.

A common vascular access device is a catheter that is inserted into a patient's vein. The catheter length may vary from a few centimeters for peripheral access to many centimeters for central access. The catheter may be inserted transcutaneously or may be surgically implanted beneath the patient's skin. The catheter, or any other vascular access device attached thereto, may have a single lumen or multiple lumens for infusion of many fluids simultaneously. A group of vascular access and other devices used to access the vasculature of a patient may be collectively referred to as an extravascular system.

One example of an extravascular system including a catheter is the BD NEXIVA™ Closed IV (intravenous) Catheter System, by Becton, Dickinson and Company. This system includes an over-the-needle, peripheral intravascular catheter made from polyurethane, another catheter used as an integrated extension tubing with a Y adapter and slide clamp, a vent plug, a Luer access port, and a passive needle-shielding mechanism.

The design of the BD NEXIVA™ IV catheter can be described as a closed system since it protects clinicians or operators from blood exposure during the catheter insertion procedure. Since the needle is withdrawn through a septum that seals, after the needle has been removed and both ports of the Y adapter are closed, blood is contained within the NEXIVA™ device during catheter insertion. The pressure exerted on the needle as it passes through the septum wipes blood from the needle, further reducing potential blood exposure. The slide clamp on the integrated extension tubing is provided to eliminate blood exposure when the vent plug is replaced with another vascular access device such as an infusion set connection or a Luer access port.

A current procedure of initiating the use of an extravascular system such as the BD NEXIVA™ Closed IV Catheter System is as follows. A device operator will insert the needle into the vasculature of a patient and wait for flashback of blood to travel into the device to confirm that the needle is properly located within the vasculature of the patient. The blood travels into and along the catheter of the device because a vent plug permits air to escape the device as blood enters the device. After an operator confirms proper placement, the operator clamps the catheter to halt the progression of blood through the catheter, removes the vent plug, replaces the vent plug with another vascular access device such as an infusion set connection or a Luer access port, unclamps the catheter, flushes the blood from the catheter back into the vasculature of the patient, and re-clamps the catheter.

Many current procedures like the procedure described above present challenges that need to be overcome. For example, the procedure may include an unnecessary number of steps and amount of time to simply insert and prepare an extravascular system for use within the vasculature of a patient. Further, by removing the vent plug, the fluid path of the system is temporarily exposed to potential contamination from the external environment of the extravascular system.

Rather than using a vent plug, some operators attempt to solve the problem above by simply loosening a Luer access device and permitting air to escape from the system during flashback and then tightening the Luer access device to stop blood from advancing along the catheter. Unfortunately, this procedure is also prone to user error, a lack of consistent and accurate control of blood flow through the system potentially leading to blood exposure and loss of body fluids, and unnecessary risk of contamination.

Thus, what are needed are improvements to many of the systems and methods described above. Such systems and methods can be improved by providing more efficient extravascular venting systems and methods.

SUMMARY OF THE INVENTION

The present invention has been developed in response to problems and needs in the art that have not yet been fully resolved by currently available extravascular systems, devices, and methods. Thus, these systems, devices, and methods are developed to provide more efficient extravascular venting systems and methods.

According to one aspect, a medical device is provided having a first vascular access device, including a luer integrated air venting system, having a female luer fitting having a distal and proximal end and a passage extending between ends, a venting mechanism located within the female luer fitting and a fluid diverter located within the vent mechanism. The venting mechanism providing communication between the vascular access device and ambient surroundings, wherein the venting mechanism permits an outflow of air from the vascular access device to the ambient surroundings through the venting mechanism, and wherein the venting mechanism substantially prevents an outflow of fluid from the vascular access device to the ambient surroundings through the venting mechanism.

The venting mechanism may include a venting plug. The venting plug can be a cylinder having a distal end and proximal end, a passage extending between ends and with at least one projection at the distal end. The at least one projection can be an indent on an internal surface of the projection. The venting mechanism may be a porous hydrophobic material or a porous material with a hydrophobic surface.

The fluid diverter is moveable within the venting mechanism from a proximal venting position where fluid cannot flow past the fluid diverter in the passage to a distal locking position where fluid can flow through the passage around the fluid diverter. The fluid diverter may be a disc wherein the disc forms a fluid seal in the passage of the venting plug in the proximal venting position.

The medical device may also include a second vascular access device having a male luer fitting, wherein the female luer fitting (of the first vascular access device) is mated with the male luer fitting to connect the first and second vascular devices, and wherein the venting mechanism is located between the female luer fitting and the male luer fitting. The female luer fitting may have a recess for retaining said venting mechanism within the female luer fitting. The first and said second vascular access devices may include at least one catheter.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

DETAILED DESCRIPTION OF THE INVENTION

The invention is a luer integrated air venting system with a self-venting mechanism that permits escape of air during use which, typically, also prevents an outflow of fluid, such as blood. As used herein, venting mechanism indicates one or more features or elements that provide venting of air, but which, typically, prevent fluid from passing through. The term "proximal" is used to denote a portion of a device which, during normal use, is nearest the user and furthest from the patient. The term "distal" is used to denote a portion of a device which, during normal use, is farthest from the user wielding the device and closest to the patient.

This invention is suitable for use in any closed system luer connection application in which venting can facilitate self priming, one example of a suitable application is an extravascular system, such as a Closed Intravenous (IV) Catheter System.

It should be noted that the vent media could be, for example, a distinct physical element such as a plug or insert, a integral portion of a device that has been treated such as by laser drilling or has been formed in whole or in part from a porous material, or a coating, layer, etc. formed by disposing a material onto the device, e.g., by dipping, coating, spraying or the like.

Figure 1:
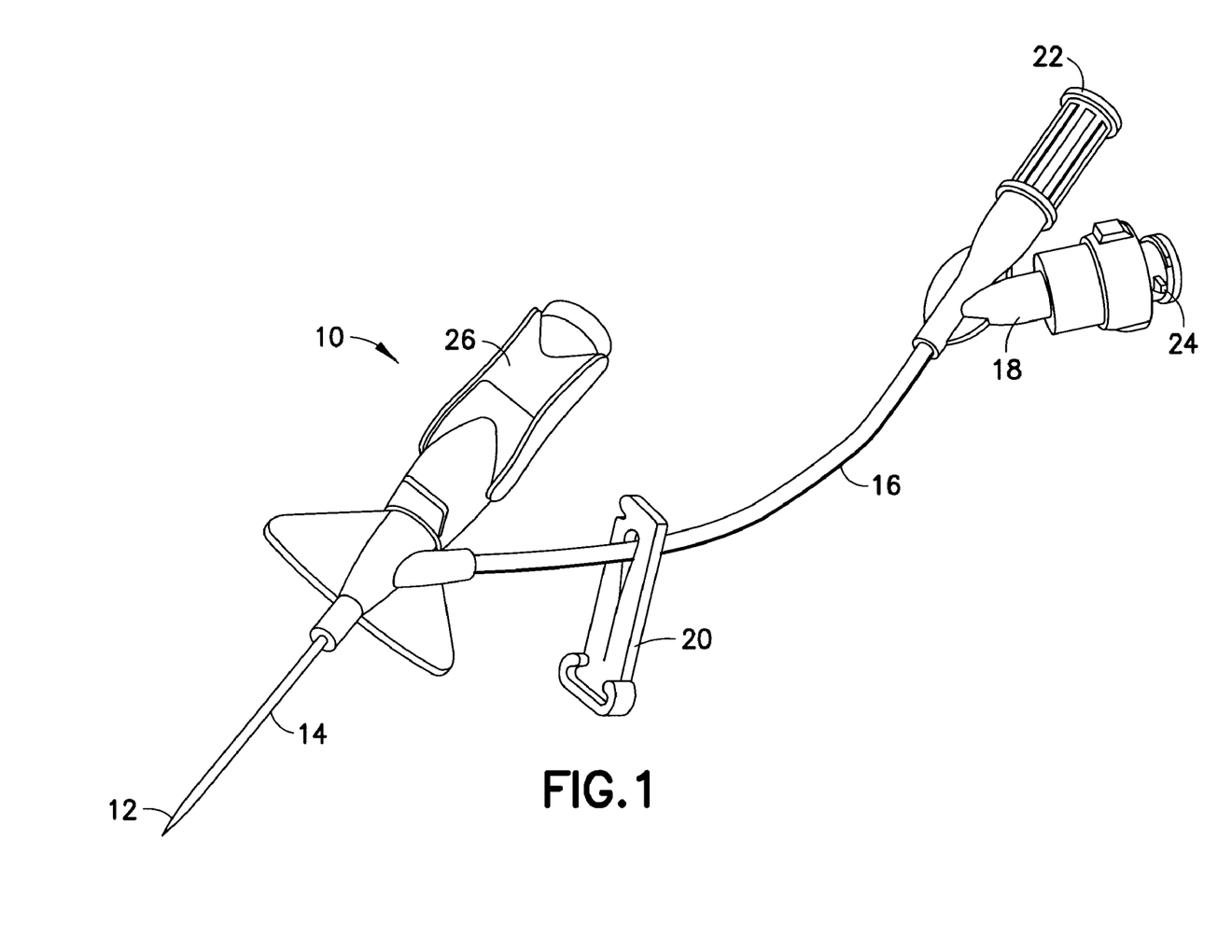
FIG. 1 is a perspective view of an extravascular system.

A prior art extravascular system [in accordance with the subject invention] is shown in FIGS. 1 to 4, an extravascular system 10, such as the BD NEXIVA™ Closed IV (intravenous) Catheter System, by Becton, Dickinson and Company, is used to communicate fluid with the vascular system of a patient. An example of the system 10, as shown in FIG. 1, includes an intravascular needle 12; an over-the-needle, peripheral intravascular catheter 14 made from polyurethane; an integrated extension tubing 16 (also referred to herein as a catheter) with a Y adapter 18 and slide clamp 20; a vent plug 22; a Luer access port 24; and a passive needle-shielding mechanism 26. Any adapter used to connect two or more vascular access devices may be used in place of the Y adapter 18.

The system 10 is a closed system since it protects clinicians or operators from blood exposure during the catheter 14 insertion procedure. Since the needle 12 is withdrawn through a septum that seals after the needle 12 has been removed and both ports of the Y adapter 18 are closed, blood is contained within the system 10 during catheter 14 insertion. The pressure exerted on the needle 12 as it passes through the septum wipes blood from the needle 12, further reducing potential blood exposure. The slide clamp 20 on the integrated extension tubing 16 is provided to eliminate blood exposure when the vent plug 22 is replaced with another vascular access device such as an infusion set connection or another Luer access port 24.

As mentioned above, a current procedure of initiating the use of the prior art extravascular system 10 is as follows. A device operator will insert the needle 12 into the vasculature of a patient and wait for flashback of blood to travel into the system 10 to confirm that the needle 12 is properly located within the vasculature of the patient. The blood travels into and along the catheter 14 in the space between the needle 12 and the catheter 14. This occurs because a vent plug 22 permits air to escape the system 10 as blood enters the system 10. After an operator confirms proper placement, and after adequate venting of the system 10 has occurred, the operator clamps the catheter 16 to halt the progression of blood through the catheter 14, removes the vent plug 22, replaces the vent plug 22 with another vascular access device such as an infusion set connection or a Luer access port similar or identical to Luer access port 24, unclamps the catheter 16, flushes the blood from the catheter 14 back into the vasculature of the patient, and re-clamps the catheter 16. Alternate vents and venting procedures are desired and will be discussed with reference to the figures following FIG. 1.

Figure 2:
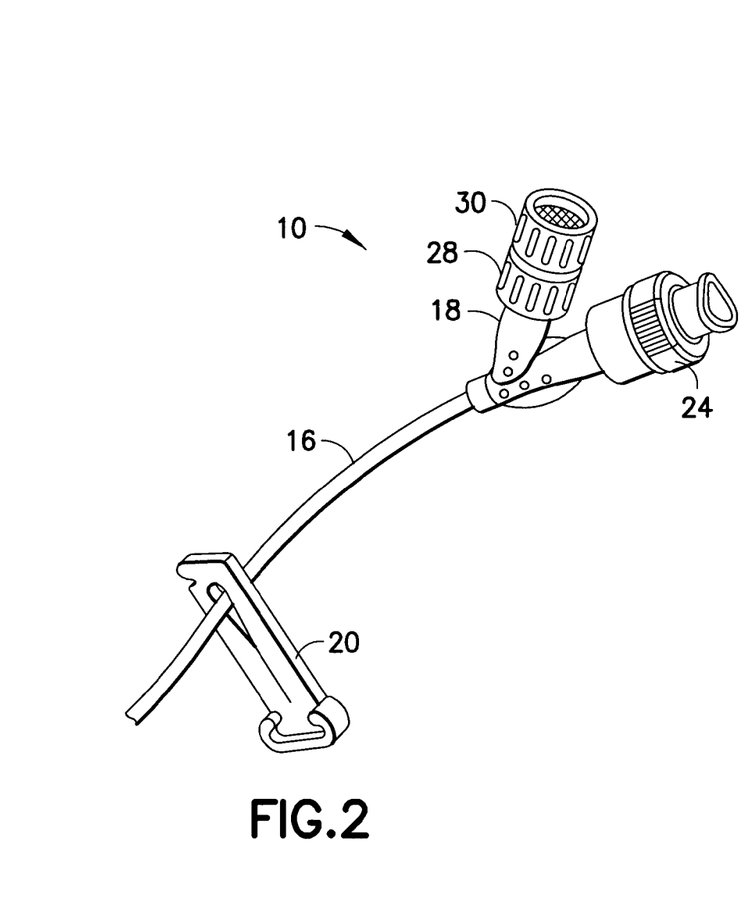
FIG. 2 is a perspective view of an extravascular system having an adapter with a ventable end cap and removable vent plug.

Referring now to FIG. 2, the extravascular system 10 includes a ventable end cap 28 and a vent plug 30. The removable vent plug 30 is removably attached to the ventable end cap 28 and permits air venting of the extravascular system 10. The ventable end cap 28 is in turn attached to an adapter 18 which is secured to a catheter 16 having a slide clamp 20. A valve or Luer access device 24 may also be attached to the adapter 18.

Figure 3:
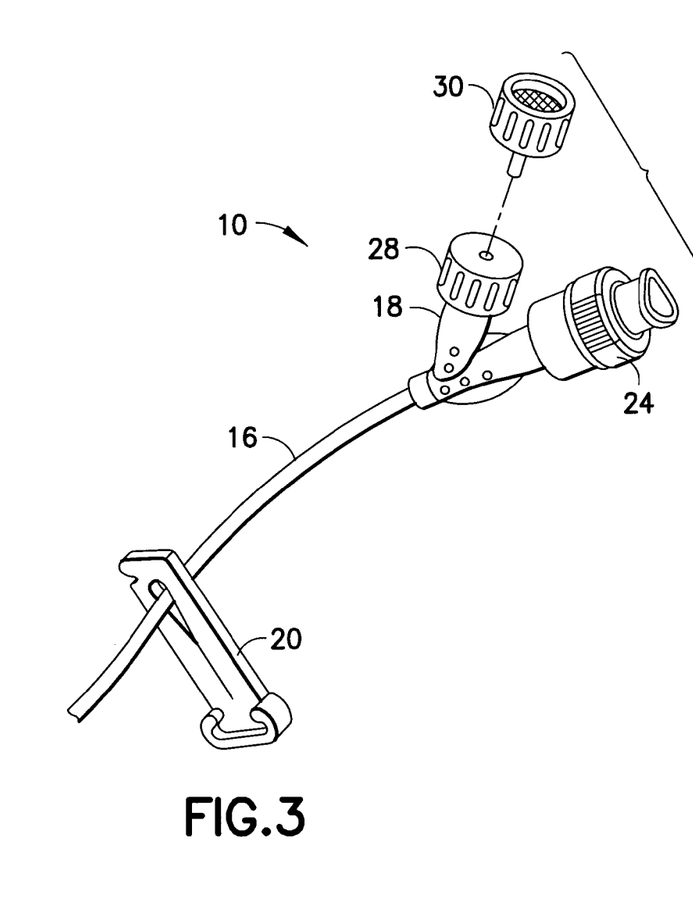
FIG. 3 is a perspective view of the extravascular system of FIG. 2 with the removable vent plug removed.

Referring now to FIG. 3, the prior art extravascular system 10 of FIG. 2 is shown with the vent plug 30 removed from the closed ventable end cap 28. After removal of the vent plug 30, the ventable end cap 28 is sealed. In its closed or sealed position, the ventable end cap 28 permits an operator of the system 10 to use the system after adequate venting and flashback of blood in order to ensure proper placement of the system 10 within the vasculature of a patient.

Figure 4:
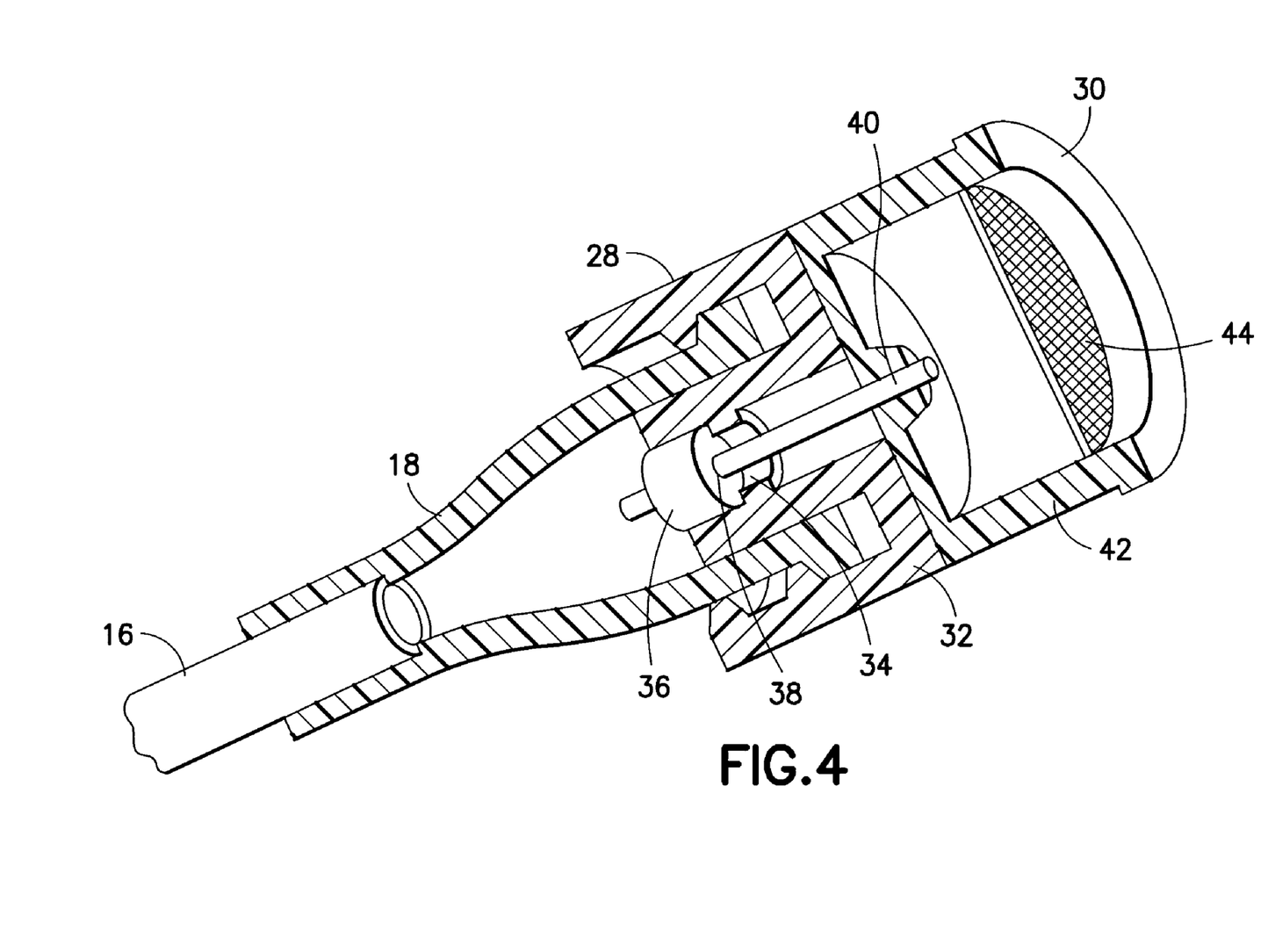
FIG. 4 is a cross section view of the adapter, ventable end cap, and removable vent plug of FIGS. 2 and 3.

Referring now to FIG. 4, a cross section perspective view of the prior art removable vent plug 30, ventable end cap 28, adapter 18, and catheter 16 is shown. The ventable end cap 28 includes a body 32 having an open channel 34 containing an elastomeric septum 36. The septum 36 has a very small access hole 38 that is sealed under compression in the end cap 28 assembly. The septum hole 38 allows a hollow cannula 40 from the removable vent plug 30 to pass, thereby, providing communication between the atmospheric pressure and the venus pressure of a patient and allowing air to vent and blood to flashback and be visible up the extension tubing 16 or other catheters attached to the extravascular system 10. The vent plug 30 includes a body 42, the attached cannula 40, and an air permeable material 44 or other air filter. The air permeable material 44 allows airflow to pass but prevents fluid from passing. This material 44 may be hydrophobic or hydrophilic and may be a glass, polyethylene terephthalate (PET), a microfiber material, or other synthetic material made of high-density polyethylene fibers, such as TYVEK® material from DuPont.

The prior art system 10 described with reference to FIGS. 2 through 4 allows an integrated catheter system to vent while remaining closed, thereby allowing flashback visualization of blood without exposing a physician to the blood. The system 10 can easily be added to an existing integrated catheter system with a Luer adapter to simplify and reduce the number of steps during administration of a closed system integrated catheter such as the BD Nexiva™ System. Use of this system 10 eliminates the need to open the catheter system between removal of the traditional vent plug 22 (shown in FIG. 1) and subsequent application of an end cap or other vascular access device such as a Luer access device 24. Thus, the ventable end cap 28 and vent plug 30 maintain a closed system 10 at all times, and remove many of the steps described above with reference to FIG. 1 with exception of the step of removing the vent plug 30 and flushing the system 10.

According to embodiments of the invention, this step of removing the vent plug 30 is removed/negated while allowing an integrated catheter system to vent while remaining closed. One embodiment of the invention is shown in FIGS. 5 to 10.

Figure 5:
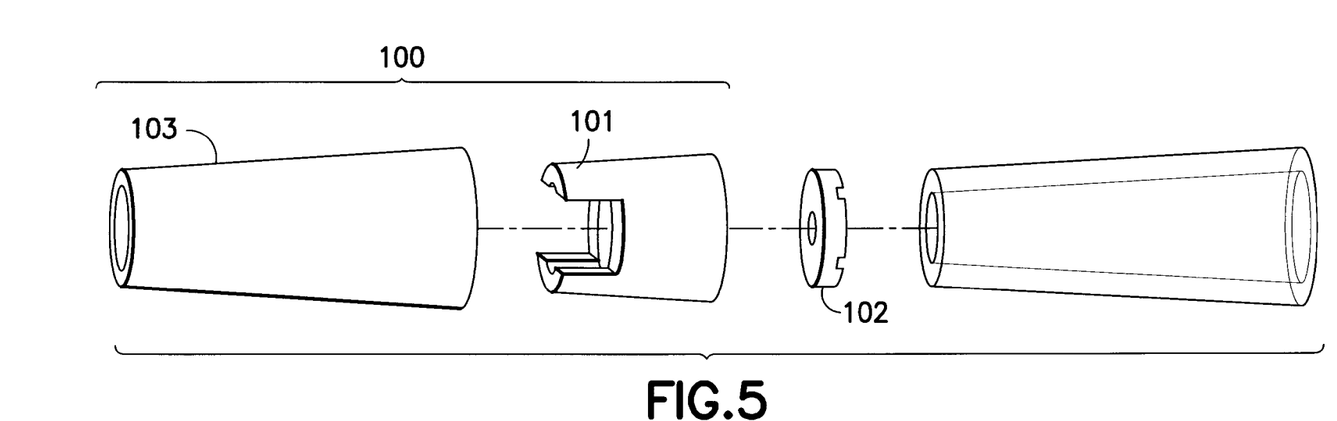
FIG. 5 is an exploded perspective view of an embodiment of the invention.
Figure 6:
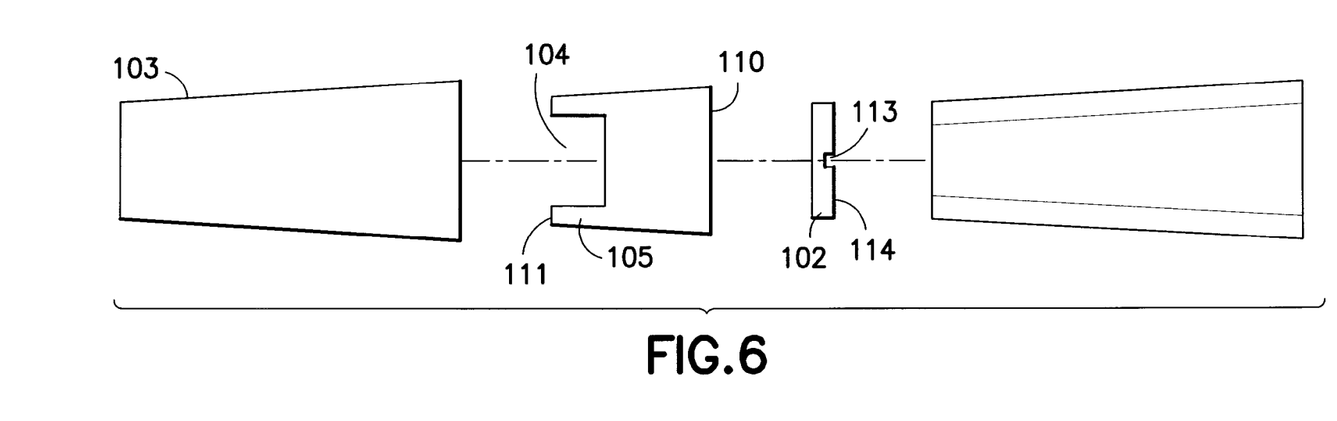
FIG. 6 is an exploded side view of an embodiment of the invention.
Figure 7:
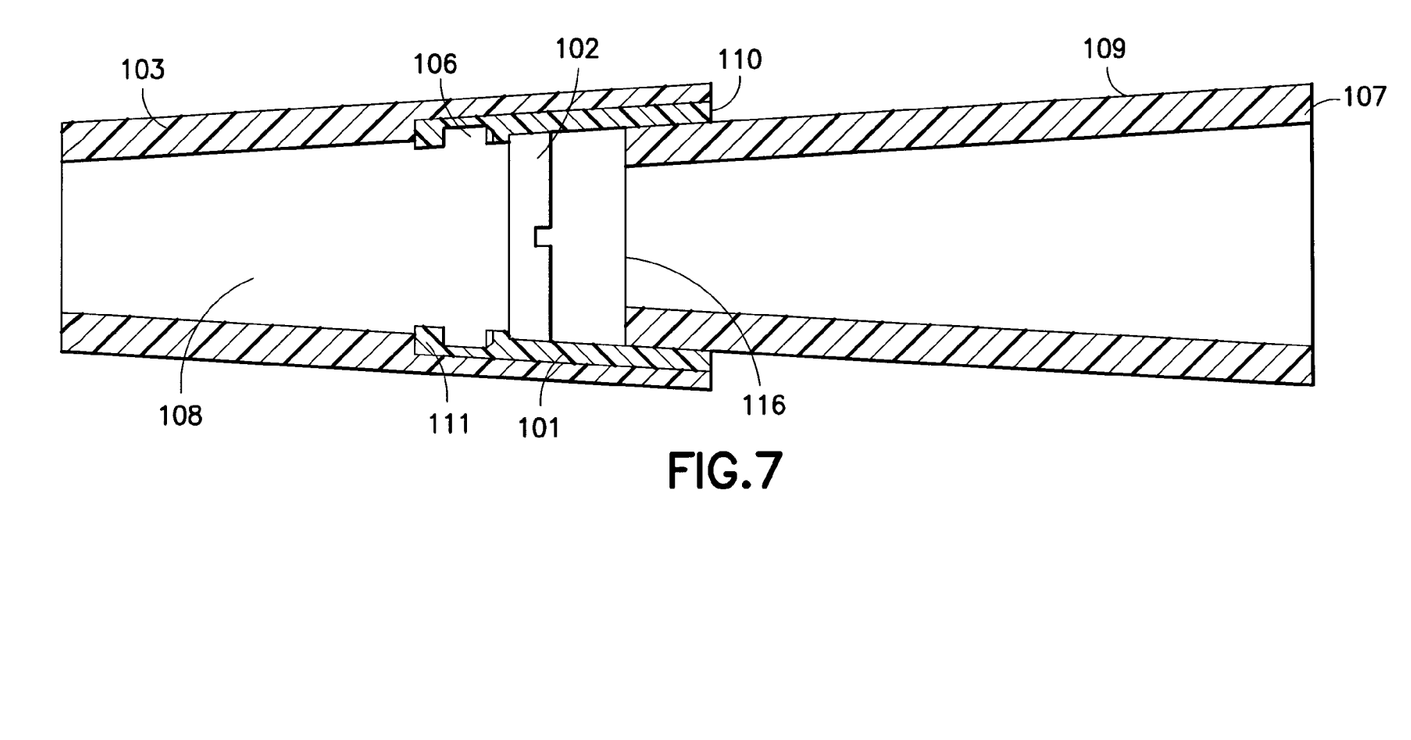
FIG. 7 is a cross section view of the female to male luer interface in an embodiment of the invention, with the fluid diverter in the proximal venting position.
Figure 8:
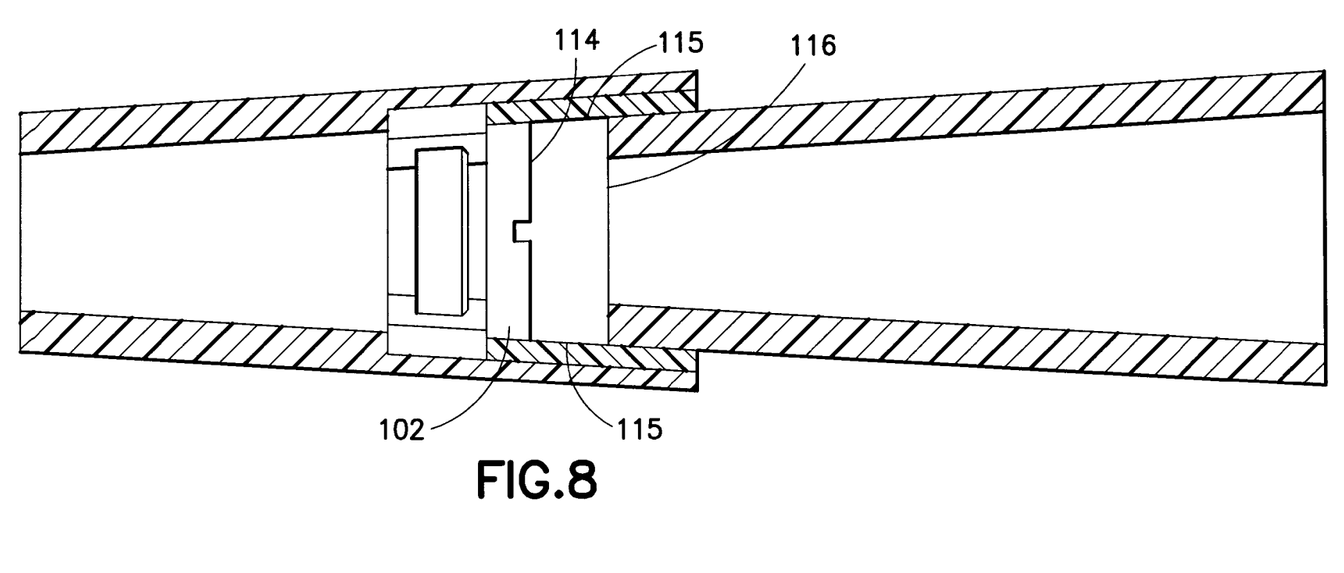
FIG. 8 is a cross section view of FIG. 7 rotated 90 degrees.

FIGS. 5 and 6 show an embodiment of a luer integrated air venting system 100 that includes a modified female luer 103, a venting plug 101, and a fluid diverter 102 which can be used in place of the Y adapter 18 in suitable first vascular access device (e.g. an integrated catheter system). Venting plug 101 is tubular in shape with two cut outs 104 thus creating two projections 105 at the distal end 111 of venting plug 101. The inner surface of each projection 105 has an indent 106 (as seen in FIGS. 7 and 8). Fluid diverter 102 is a rigid disc typically made from a thermoplastic material. The diverter 102 can have two channels 113 formed on proximal face 114.

FIGS. 7 and 8 shows a mating male luer 107 of a second vascular access device connected to the luer integrated air venting system 100 with the fluid diverter 102 in the proximal venting position. Vent plug 101 is located between the interface of the modified female luer 103 and the male luer 107, and provides gaseous communication between female luer passage 108 and the ambient surroundings. The venting plug 101 acts as a spacer and forms an interference fit with the male luer taper 109.

In the proximal venting position, fluid diverter 102 forms an interference fit of sufficient magnitude with the inside surface of the vent plug 101 to limit further proximal movement when in use. Optionally a flange on the inner surface of the venting plug (not shown) can also be used to prevent any further proximal movement of fluid diverter 102. Air is able to flow from the female luer passage 108 through the vent plug 101 at any point distal of the fluid diverter 102 to the surrounding atmosphere at the proximal end 110 of vent plug 101. On insertion of needle 12 into the vasculature of a patient the air present within system 10 in advance of the liquid will be expelled through the vent plug 101, until the liquid comes in contact with the vent plug 101 at which point the vent material seals [typically at area 125] and a fluid seal is formed within the female luer by the combination of the sealed vent plug material and the fluid diverter 102.

As discussed above, typically an infusion is performed by connecting a second vascular access device containing a liquid such as a medicament, pharmaceutical, or blood product for example, to the first vascular access device (an integrated catheter system). On the infusion of the liquid from the second vascular access device the air present in the system proximal to male luer is then vented, in this embodiment, by flowing through the vent plug 101 at the internal surface section 115 which is intermediate the proximal face 114 of the fluid diverter 102 (and which has not yet been in contact with the liquid) and the distal end of the male luer 116, until the liquid from the second vascular access device comes in contact with the vent plug 101, the liquid activates the self sealing material of the vent plug 101 and prevents leakage out of the luer connection.

Figure 9:
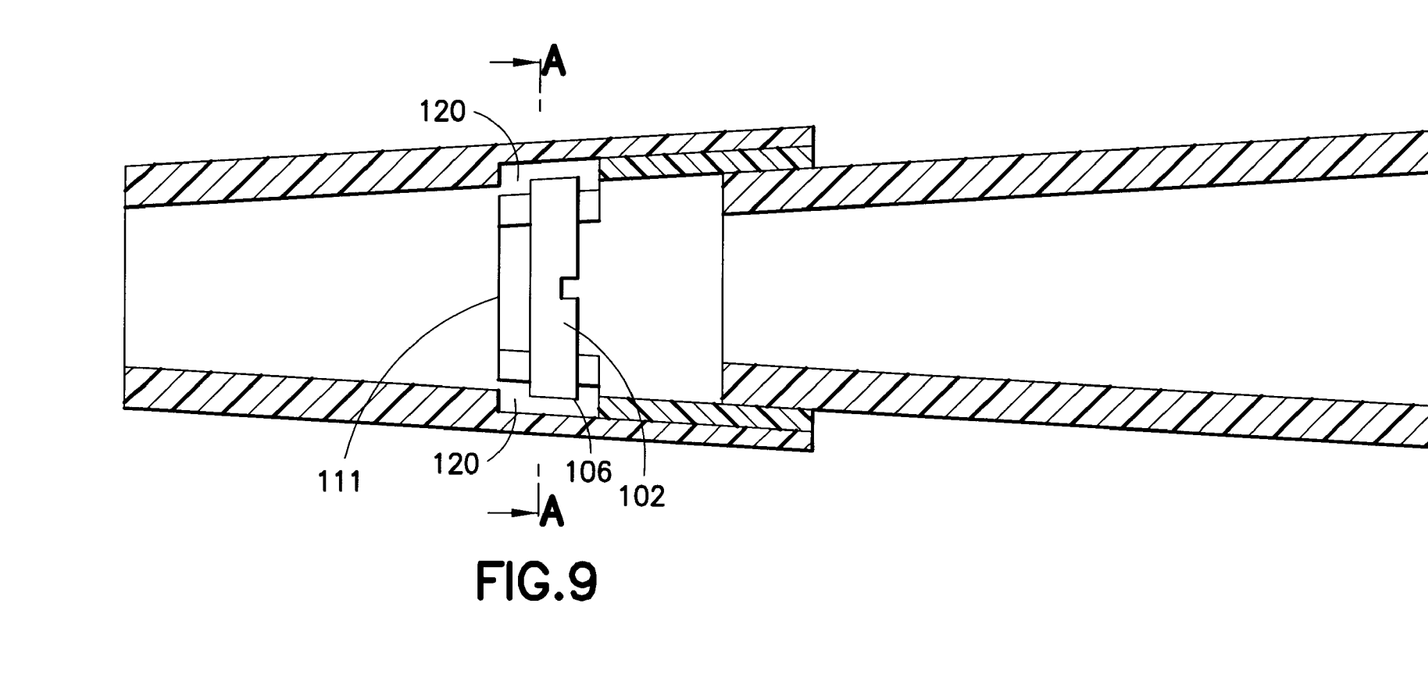
FIG. 9 is a cross section view of the female to male luer interface in an embodiment of the invention, with the fluid diverter in the distal locking position.
Figure 10:
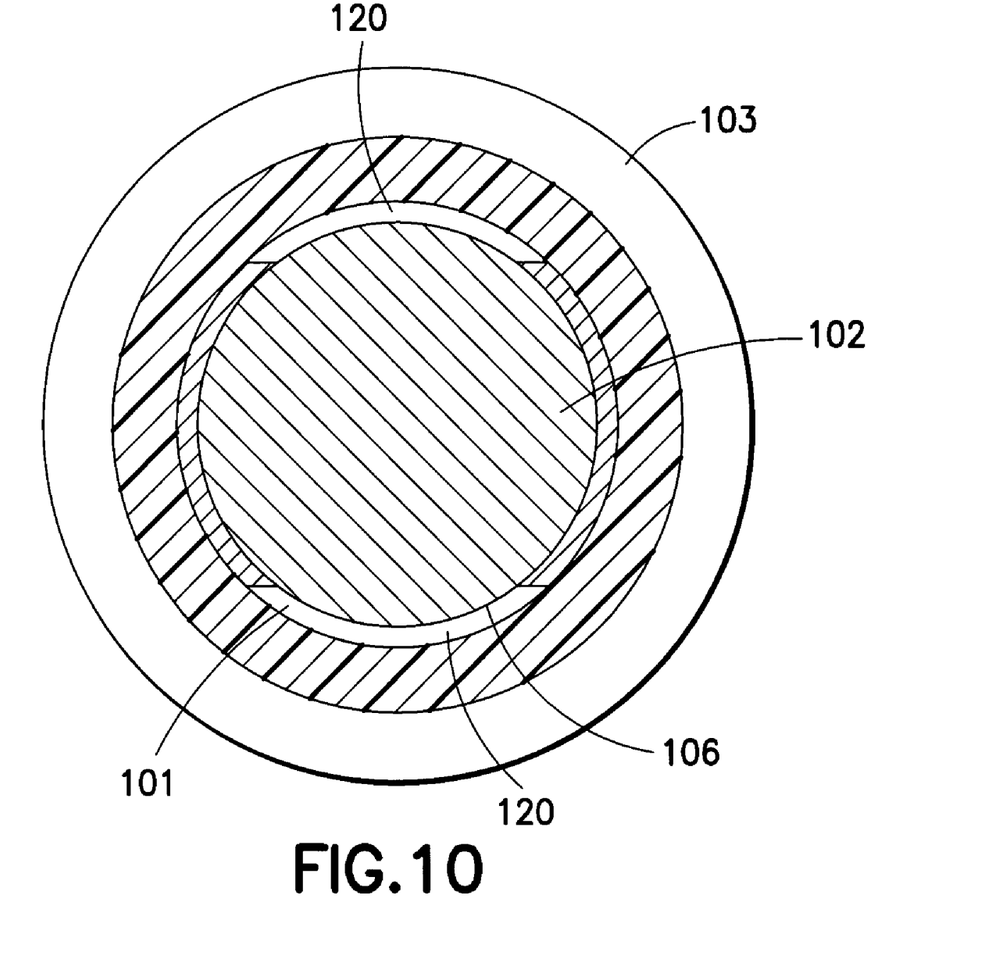
FIG. 10 is a cross section view of FIG. 9 from the aspect of A-A.

The liquid continues to be directed distally after the plug 101 seals. As the internal pressure of the liquid from the second vascular access device proximal the male luer increases, the previously constrained fluid diverter 102 is forced distally in direction Z (see FIG. 9) forward by fluid pressure and becomes retained by indents 106 at the distal end 111 of vent plug 101. FIGS. 9 and 10 show diverter disk 102 in a distal locking position. A fluid path is then opened by the combination of cut outs 104 in vent plug 101 and a recess 120 in the internal surface of female luer 103 that allows for bidirectional free fluid flow around diverter disk 102 once the fluid diverter 102 is in the distal locking position. Thus the invention allows an integrated catheter system to vent while remaining closed without the additional step of removing a vent plug.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A medical device comprising:
   a first vascular access device comprising a luer integrated air venting system, having
     a female luer fitting having an inner surface, a distal end, a proximal end, and a passage extending between said ends;
     an annular venting mechanism located within said passage of said female luer fitting and seated against the inner surface of the female luer, a distal end of the annular venting mechanism having a cutout in fluid communication with a passageway extending through the annular venting mechanism; and
     a fluid diverter located within said passageway of said annular vent mechanism, said annular venting mechanism providing communication between said vascular access device and ambient surroundings, wherein said venting mechanism permits an outflow of air from said vascular access device to said ambient surroundings through said annular venting mechanism, and wherein said annular venting mechanism substantially prevents an outflow of fluid from said vascular access device to said ambient surroundings through said annular venting mechanism.

2. The medical device of claim 1, wherein said annular venting mechanism further comprises a venting plug.

3. The medical device of claim 2, wherein said venting plug further comprises at least one projection at said distal end.

4. The medical device of claim 3, wherein said at least one projection further comprises an indent on an internal surface of said projection.

5. The medical device of claim 1, wherein said annular venting mechanism comprises a porous hydrophobic material or said annular venting mechanism comprises a porous material with a hydrophobic surface.

6. The medical device of claim 1, wherein said fluid diverter is moveable within said passageway of said annular venting mechanism from a proximal venting position where fluid is prevented from flowing past said fluid diverter in said passageway, to a distal locking position where fluid is permitted to flow through said passageway around said fluid diverter.

7. The medical device of claim 1, wherein said fluid diverter further comprises a disc.

8. The medical device of claim 1, further comprising a second vascular access device having a male luer fitting, wherein said female luer fitting is mated with said male luer fitting to connect said first and second vascular devices, and wherein said annular venting mechanism is interposedly located between said female luer fitting and said male luer fitting.

9. The medical device of claim 1, wherein said female luer fitting further comprises a recess for retaining said annular venting mechanism within said female luer fitting.

10. The medical device of claim 8, wherein at least one of said first and said second vascular access devices is a catheter.

11. A vascular access device comprising:
a female luer fitting having an inner surface;
an annular venting mechanism having an inner surface, an outer surface, a proximal portion, and a distal portion, the annular venting mechanism being disposed within the female luer fitting such that the outer surface of the annular venting mechanism is seated against the inner surface of the female luer fitting, the venting mechanism having a passage extending therethrough, the distal portion having a cut out in fluid communication with the passage;
a fluid diverter disposed at least partially within the passage of the venting mechanism and being movable from a first position within the venting mechanism to a second position within the venting mechanism, the fluid diverter blocking fluid flow through the passage when in the first position and permitting fluid flow through the passage when in the second position.

12. The vascular access device of claim 1, wherein the distal portion of the annular venting mechanism further includes a projection.

13. The vascular access device of claim 8, wherein the projection includes an indent on an internal surface of the projection.

14. The vascular access device of claim 9, wherein the second position of the fluid diverter is within the indent on an internal surface of the projection.

15. The vascular access device of claim 10, wherein the distal portion has a second projection, the second projection having an indent on an internal surface of the projection, and the second position of the fluid diverter is also within the indent on an internal surface of the second projection.

16. The vascular access device of claim 1, wherein the annular venting mechanism permits an outflow of air from the vascular access device to the ambient surroundings, and substantially prevents an outflow of fluid from the vascular access device to the ambient surroundings.

17. The vascular access device of claim 1, wherein the annular venting mechanism comprises a porous hydrophobic material or a porous material with a hydrophobic surface.

18. A vascular access device comprising:
a female luer fitting having an inner surface;
an annular venting mechanism having an inner surface, an outer surface, a proximal portion, and a distal portion, the annular venting mechanism being disposed within the female luer fitting such that the outer surface of the annular venting mechanism is seated against the inner surface of the female luer fitting, the venting mechanism having a passage extending therethrough, the distal portion having a cut out in fluid communication with the passage;
a fluid diverter disposed at least partially within the passage of the venting mechanism and being movable from a first position to a second position, wherein the first position is within the proximal portion of the annular venting mechanism, and the second position is within the distal portion of the annular venting mechanism adjacent the cutout, the fluid diverter further blocking fluid flow through the passage when in the first position and permitting fluid flow through the cutout and the passage when in the second position.

19. The vascular access device of claim 14, wherein the annular venting mechanism permits an outflow of air from the vascular access device to the ambient surroundings, and substantially prevents an outflow of fluid from the vascular access device to the ambient surroundings.

20. The vascular access device of claim 14, wherein the annular venting mechanism comprises a porous hydrophobic material or a porous material with a hydrophobic surface.

* * * * *